United States Patent [19]

Livingston

[11] Patent Number: 5,475,031
[45] Date of Patent: Dec. 12, 1995

[54] DISCOVERY OF A VALUABLE PROPERTY FOR SUCCINIC ACID AND OTHER INTERMEDIARY METABOLITES

[76] Inventor: William H. Livingston, R-223 N. 13th St., Artesia, N.M. 88210

[21] Appl. No.: 115,814

[22] Filed: Sep. 3, 1993

[51] Int. Cl.[6] .................................................. A61K 31/19
[52] U.S. Cl. ........................ 514/574; 514/811; 514/869
[58] Field of Search ................................. 514/574, 811, 514/869

[56] References Cited

U.S. PATENT DOCUMENTS 3,694,549  9/1972  Livingston ............................. 514/574
5,025,037  6/1991  Livingston ............................. 514/574

OTHER PUBLICATIONS

Voet et al, Biochemistry, published by John Wiley & Sons, N.Y., N.Y., pp. 521–527 (1990).
Mathews et al., Biochemistry, published by the Benjamin/Cummings Publishing Company, Inc., N.Y., N.Y., pp. 485–491 (1990).

*Primary Examiner*—Ronald W. Griffin

[57] ABSTRACT

This invention relates to the use of the succinic acid molecule to stimulate the Citric Acid Cycle in humans and animals and thus relieve those metabolic disorders caused by a deficiency in the Citric Acid Cycle in humans and animals.

1 Claim, No Drawings

DISCOVERY OF A VALUABLE PROPERTY FOR SUCCINIC ACID AND OTHER INTERMEDIARY METABOLITES

CROSS REFERENCE OR DRAWINGS

Drawings none, reference U.S. Pat. No. 3,694,549, and U.S. Pat. No. 5,025,037.

SUMMARY

Discovered a property of the Succinic Acid Molecule.

BACKGROUND OF THE INVENTION

Succinic Acid has been included in the formulations used in the referenced patents, along with other intermediary metabolites. During this work a new property was accidentally discovered. That important discovery is that intermediary metabolites have the ability to penetrate the mucous membranes of the mouth and be absorbed immediately, and stimulate a deficient Citric Acid Cycle. This property is especially noticeable for oxoaloactic acid, and succinic acid. Succinic acid is cheaper and more stable. The method of discovery is as follows: It was observed that alcohol is burned up by metabolism in the Citric Acid Cycle. A number of experiments were conducted first by the inventor, and then with others. Individuals who had consumed too much alcohol, were asked to read a title on a book about 8 feet away When they were unable to read the title. They drank a glass of water containing succinic acid or Oxaloacetic acid. By the time they set the glass down, they would immediately be able to read the title of the book. This experiment was repeated over 100 times, and 95% of the people had the same result. Some of the people could not read the title when they were sober, because of their eye sight. The results of this test demonstrates a new and useful property for the succinic acid molecule and other intermediary metabolites that have this property. Citric Acid has some of these properties, but not as dramatic as oxaloactic acid and succinic acid. It is speculated that the size of the succinic acid molecule contributes to its ability to penetrate the mucous membranes of the mouth. Dogs that have high Blood Urea Nitrogen (BUN) due to kidney failure, responded immediately to oral Succinic Acid, their attitude changed, and they had more energy and apparently felt better immediately. Their SGOT, serium glutamic, oxaloacetic transaminase, levels dropped within 24 hours.

"Much of the lack of medical application in the field of, intermediary metabolism, is due to early cellular scientist who made two miss-statements that were quoted and these quotes misled those who followed, these miss statements are:

1. That, "fats burn in the fire of carbohydrates". This is not true, actually fats and carbohydrates burn in the furnace of the Citric acid Cycle. Citric Acid Cycle metabolites are derived from the deamination of protein.
2. "Gluconeogensis:" This word is misleading, because there is nothing beneficial when protein is broken down into intermediary metabolites, and then oxalacetic acid loses a methyl group and is converted to pyruvic acid, and Citric Acid Cycle is lost. When enough Citric Acid Cycles are lost, the patient loses 90% of its ability to produce energy, and eventually goes into a coma.

These two misleading statements have made intermediary metabolism hard to understand. Our understanding and clinical experience of the information guided us in developing new and useful uses for intermediary metabolites that are not understood by most people knowledgeable in the art.

A saturated solution of succinic acid in water is orally used to stimulate the citric acid cycle in animals and in humans. The dose is variable depending on the condition and weight of the animal. The dose has varied from one cc to 100 cc of water saturated with succinic acid. This solution is prepared by adding succinic acid crystals to sterile water the container is shaken, and the excess succinic acid is allowed to settle out. Then the superannuate solution is super saturated, this is the material, used orally, to stimulate a deficient Citric Acid Cycle. Succinic Acid and Oxaloacetic acid have been used intravenously to stimulate a deficient Citric Acid Cycle. Oral administration is safer and easier. Inert flavors and sweeteners may be added to make a mixture that is more palatable, and this mixture or the original solution may be added to compatible foods.

DESCRIPTION AND ADVANTAGE OF THE INVENTION

I therefore, particularly point out and distinctly claim as my discovery that succinic acid, Oxaloacetic acid, and to a lesser degree all intermediary metabolite have the ability to penetrate mucous membranes when administered orally and immediately enter the blood stream and stimulate the Citric Acid Cycle.

I claim:

1. A method for immediately stimulating a deficient Citric Acid Cycle in humans and animals which comprises administering to said humans or animals in need thereof an oral therapeutic dose of succinic acid or other intermediary metabolites of the Citric Acid Cycle or mixtures thereof which have the ability to penetrate the mucous membranes of the mouth and enter the blood stream intact, and relieve those metabolic disorders caused by a deficiency in the Citric Acid Cycle.

* * * * *